United States Patent
Guskey et al.

(10) Patent No.: US 11,160,741 B2
(45) Date of Patent: Nov. 2, 2021

(54) PERSONAL CARE COMPOSITIONS AND USES

(71) Applicant: The Procter & Gamble Company, Cincinnati, OH (US)

(72) Inventors: Gerald John Guskey, Symmes Township, OH (US); Shannon Dale Wagers, Liberty Township, OH (US); Edward Dewey Smith, III, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 266 days.

(21) Appl. No.: 16/286,949

(22) Filed: Feb. 27, 2019

(65) Prior Publication Data

US 2019/0262249 A1 Aug. 29, 2019

(30) Foreign Application Priority Data

Feb. 27, 2018 (EP) ..................................... 18158738

(51) Int. Cl.
*A61K 8/00* (2006.01)
*A61K 8/46* (2006.01)
(Continued)

(52) U.S. Cl.
CPC ................ *A61K 8/463* (2013.01); *A61K 8/19* (2013.01); *A61K 8/23* (2013.01); *A61K 8/33* (2013.01);
(Continued)

(58) Field of Classification Search
CPC .......... A61K 8/463; A61K 8/19; A61K 8/362; A61K 8/442; A61Q 19/10
See application file for complete search history.

(56) References Cited

U.S. PATENT DOCUMENTS

2006/0019846 A1 1/2006 Fan
2006/0019847 A1 1/2006 Fan et al.
(Continued)

FOREIGN PATENT DOCUMENTS

WO WO200062755 A1 10/2000
WO WO2009090617 A2 7/2009
WO WO2009116076 A2 9/2009

OTHER PUBLICATIONS

International Search Report and Written Opinion of the International Searching Authority, PCT/US2019/019550, dated Apr. 15, 2019, 13 pages.
(Continued)

*Primary Examiner* — Necholus Ogden, Jr.
(74) *Attorney, Agent, or Firm* — Angela K. Haughey (57) ABSTRACT

Described herein, a personal care composition and its uses, wherein the personal care composition comprises a surfactant system, wherein the surfactant system comprises: from 3% to 15% of an anionic surfactant by weight of the composition, wherein the anionic surfactant is sodium laureth(1) sulfate SLE1S, from 1% to 15% of one or more cosurfactants by weight of the composition; from 0.10% to 5.0%, from 0.20% to 2.5%, from 0.25% to 1.75%, from 0.50% to 1.75%, of one or more salts of Formula I by total weight of the composition, M----A                Formula I wherein A is an anion selected from the group consisting of sulfate and citrate;
wherein M is a cation selected from the group IA alkali metal, wherein M is selected from the group consisting of lithium, sodium, potassium, rubidium and cesium, wherein M is selected from the group consisting of lithium, sodium, and potassium; and
(Continued)

wherein the personal care composition does not comprise any metal halide, wherein the metal halide is selected from the group consisting of sodium chloride, potassium chloride, iron II or III chloride and aluminum chloride.

7 Claims, 2 Drawing Sheets

(51) Int. Cl.
    *A61K 8/19*     (2006.01)
    *A61K 8/362*     (2006.01)
    *A61K 8/37*     (2006.01)
    *A61K 8/44*     (2006.01)
    *A61Q 19/10*     (2006.01)
    *A61K 8/33*     (2006.01)
    *A61K 8/23*     (2006.01)
(52) U.S. Cl.
    CPC ............... *A61K 8/362* (2013.01); *A61K 8/37* (2013.01); *A61K 8/44* (2013.01); *A61K 8/442* (2013.01); *A61Q 19/10* (2013.01)

(56) References Cited

U.S. PATENT DOCUMENTS

| | | |
|---|---|---|
| 2006/0019858 A1 | 1/2006 | Kruse |
| 2011/0305652 A1 | 12/2011 | Hilvert |
| 2012/0164197 A1 | 6/2012 | Kitko |
| 2013/0149273 A1* | 6/2013 | Wei ................ A61K 8/8152 424/70.13 |
| 2013/0174863 A1 | 7/2013 | Marsh et al. |
| 2016/0310376 A1* | 10/2016 | Torres Rivera ........ A61K 8/416 |

OTHER PUBLICATIONS

Tang et al., Multiscale Modeling of the Effects of Salt and Perfume Raw Materials on the Rheological Properties of Commercial Thread-like Micellar Solutions, The Journal of Physical Chemistry B, 2017, 121, pp. 2468-2485.

Extended European Search Report and Search Opinion; Application No. 18158738.7; dated May 9, 2018; 8 pages.

* cited by examiner

PERSONAL CARE COMPOSITIONS AND USES

FIELD OF THE INVENTION

The present application generally relates to personal care compositions and their uses, the personal care compositions having desirable lathering and dissolution properties; and desirable rheologic properties when the surfactant system comprises sodium laureth(1) sulfate as the anionic surfactant instead of a mixture of sodium laureth(3) sulfate and sodium lauryl sulfate.

BACKGROUND OF THE INVENTION

Surfactants are widely used in consumer products, including personal care products. Many of these surfactant solutions contain elongated micelles and are viscoelastic, which is of great importance, especially in the design of shampoos and body washes.

In most personal care compositions, anionic surfactants predominate. The simplest and most common of these anionic surfactants is sodium dodecyl sulfate (SDS). In practical applications, mixed surfactants are usually used because of the lower cost of polydisperse mixtures and their improved performance over that of the single-surfactant solutions. The addition of the ionic surfactant sodium lauryl ether sulfate (SLES) to a sodium dodecyl sulfate (SDS) solution enhances the viscosity of the personal care composition at low total surfactant concentration.

Superior interfacial tension reduction is obtained upon addition of the zwitterionic surfactant cocamidopropyl betaine (CAPB) to a sodium dodecyl sulfate (SDS) solution. Although the addition of cationic surfactants to anionic surfactants boosts viscosity enormously at low surfactant concentrations, the formation of an insoluble complex can limit the range of practicable formulations, and so it is often avoided when developing improved personal care compositions.

A commercially available personal care composition comprises sodium laureth(3) sulfate or sodium lauryl ethylene glycol sulfate (SLEnS, where n=3 is the average number of ethylene glycol repeat units) with sodium lauryl sulfate (SLS) and cocamidopropyl betaine (CAPB). When the surfactant system of the personal care composition is replaced by sodium laureth(1) sulfate (SLE1) and cocamidopropyl betaine (CAPB), the rheological properties of the personal care composition are impacted. At a low concentration of sodium chloride as the salt used in the composition, the viscosity of the personal care composition comprising sodium laureth(1) sulfate (SLE1S) and cocamidopropyl betaine (CAPB) has been increased in a relatively steeper manner for relatively low weight fraction of sodium chloride. The thickening efficiency of the surfactant system is affected such that the desired lathering and dissolution properties become compromised.

Accordingly, there is a need to optimize a personal care composition comprising sodium laureth(1) sulfate and cocamidopropyl betaine (CAPB) in terms of rheological properties.

There is a need for a personal care composition comprising sodium laureth(1) sulfate and cocamidopropyl betaine (CAPB) to provide satisfying rheological properties, lather and dissolution properties.

SUMMARY OF THE INVENTION

A personal care composition is provided and comprises:
(a) a surfactant system, wherein the surfactant system comprises:
from 3% to 15% of an anionic surfactant by weight of the composition, wherein the anionic surfactant is sodium laureth(1) sulfate SLE1S, from 1% to 15% of one or more cosurfactants by weight of the composition;
(b) from 0.10% to 5.0%, from 0.20% to 2.5%, from 0.25% to 1.75%, from 0.50% to 1.75%, of one or more salts of Formula I by total weight of the composition, M----A             Formula I wherein A is an anion selected from the group consisting of sulfate and citrate;
wherein M is a cation selected from the group 1A alkali metal, wherein M is selected from the group consisting of lithium, sodium, potassium, rubidium and cesium, wherein M is selected from the group consisting of lithium, sodium, and potassium; and wherein the personal care composition does not comprise any metal halide, wherein the metal halide is selected from the group consisting of sodium chloride, potassium chloride, iron II or III chloride and aluminum chloride.

Use of a personal care composition comprising:
(a) a surfactant system, wherein the surfactant system comprises:
from 3% to 15% of an anionic surfactant by weight of the composition, wherein the anionic surfactant is sodium laureth(1) sulfate SLE1S,
from 1% to 15% of one or more cosurfactants by weight of the composition;
(b) from 0.10% to 5.0%, from 0.20% to 2.5%, from 0.25% to 1.75%, from 0.50% to 1.75%, of one or more salts of Formula I by total weight of the composition, M----A             Formula I wherein A is an anion selected from the group consisting of sulfate and citrate;
wherein M is a cation selected from the group 1A alkali metal, wherein M is selected from the group consisting of lithium, sodium, potassium, rubidium and cesium, wherein M is selected from the group consisting of lithium, sodium, and potassium; and wherein the personal care composition does not comprise any metal halide, wherein the metal halide is selected from the group consisting of sodium chloride, potassium chloride, iron II or III chloride and aluminum chloride for decreasing the viscosity maximum and the slope value of the curve of the viscosity of the personal care composition versus the weight amount of the one or more salts by weight of the composition.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

DETAILED DESCRIPTION OF THE INVENTION

Definitions and General

In this document, including in all embodiments of all aspects of the present invention, the following definitions apply unless specifically stated otherwise.

All percentages are by weight (w/w) of the respective composition, unless otherwise specified. All ratios or percentages are weight ratios or weight percentages unless specifically stated otherwise. "% wt." means percentage by weight. References to "parts" e.g. a mixture of 1 part X and 3 parts Y, is a ratio by weight. When more than one composition is used during a treatment, the total weight to be considered is the total weight of all the compositions applied on the hair or skin simultaneously (i.e. the weight found "on head"), unless otherwise specified.

"QSP" or "q.s." means sufficient quantity for 100% or for 100 g. "+/−" indicates the standard deviation. All ranges are inclusive and combinable. The number of significant digits conveys neither a limitation on the indicated amount nor on the accuracy of the measurement.

All measurements are understood to be made at 20° C. and at ambient conditions, where "ambient conditions" means at 1 atmosphere (atm) of pressure and at 65% relative humidity, unless otherwise stated. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International.

Herein "min" means "minute" or "minutes". Herein "mol" means mole. Herein "g" following a number means "gram" or "grams". "Ex." means "example". All amounts as they pertain to listed ingredients are based on the active level ("solids") and do not include carriers or by-products that may be included in commercially available materials.

Herein, "comprising" means that other steps and other ingredients can be included in addition. "Comprising" encompasses the terms "consisting of" and "consisting essentially of". The compositions, methods, and uses of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated.

As used herein, the articles including "a" and "an" when used in a claim, are understood to mean one or more of what is claimed or described.

The terms "include," "includes," and "including," as used herein are meant to be non-limiting.

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the composition.

The term "substantially free of" as used herein means less than 1%, less than 0.8%, less than 0.5%, less than 0.3%, or less than an immaterial amount of by total weight of the composition.

The term "mixtures" as used herein is meant to include a simple combination of materials and any compounds that may result from their combination.

The term "molecular weight" or "M.Wt." as used herein refers to the weight average molecular weight unless otherwise stated. The weight average molecular weight can be measured by gel permeation chromatography ("GPC").

The term "personal care composition" as used herein refers to compositions intended for topical application to the skin or hair for cleansing.

The term "sodium laureth(n) sulfate" or "sodium lauryl ethylene glycol ether sulfate (SLEnS) as used herein refers to an abbreviate for sodium laureth sulfate comprising "n" ethoxyl groups on average. Thus, sodium laureth(1) sulfate (SLE1S) is an abbreviation for SLES with one ethoxyl group on average, but with a distribution of the number of ethoxyl groups ranging from 0 to 10. Sodium laureth(3) sulfate (SLE3S) is an abbreviation for SLES with three ethoxyl groups on average.

The term "hydrotrope" as used herein refers as a compound able to solubilize hydrophobic compounds in aqueous solutions (by means other than micellar solubilization).

Benefits of the Salt, and Optionally with the Addition of a Hydrotrope

The viscosity maximum of the salt curves of the personal care compositions of the present invention is attributed to the formation of the micellar branches.

The replacement of the surfactant system of the personal care composition comprising sodium laureth(3) sulfate (SLE3S), sodium lauryl sulfate (SLS) and cocamidopropyl betaine (CAPB) by sodium laureth(1) sulfate (SLE1S) and cocamidopropyl betaine (CAPB), has led to an alteration of the rheological properties of the personal care composition. The salt curve of the personal composition comprising sodium laureth(1) sulfate (SLE1S) and cocamidopropyl betaine (CAPB) is shifted to a lower sodium chloride salt concentration, however with a higher viscosity maximum and in a steeper manner, i.e. a relatively higher salt curve slope. In that case, the thickening efficiency of the surfactant system is affected such that the desired lathering and dissolution properties become compromised.

The desired rheological properties shall be similar or even improved with regard to the ones exhibited with the personal care composition comprising sodium laureth(3) sulfate (SLE3S), sodium lauryl sulfate (SLS) and cocamidopropyl betaine (CAPB).

The personal care composition comprising sodium laureth (1) sulfate (SLE1S) and cocamidopropyl betaine (CAPB) forms a micellar system in which relatively small micelles are formed and become elongated with the addition of sodium chloride as the salt into linear and cylindrical micelles (worm-like micellar structures). These small micelles become entangled providing more rigidity of the micellar system via addition of sodium chloride. The micellar system begins to thicken at a relatively very low weight fraction of sodium chloride compared to the referenced micellar system comprising sodium laureth(3) sulfate (SLE3S), sodium lauryl sulfate (SLS) and cocamidopropyl betaine (CAPB). The maximum viscosity at such low weight fraction of sodium chloride has increased drastically such that the personal care composition is so thick that compromised lathering or dissolution properties can be obtained. This phenomenon has been characterized further below by a salt curve having a relatively very steep slope.

It has been surprisingly found that the nature of the salt can have an impact on the micellar properties of the surfactant system of the personal care composition by modifying the packing between the surfactant head groups.

Only specific salts, optionally combined with a specific class of hydrotropes can affect the thickening efficiency of the surfactant system. By modifying the micelle formation and the packing of surfactants, it is possible to provide personal care compositions exhibiting relatively lower maximum viscosity at a higher salt weight fraction. In that case, the salt curves representing the plots of the zero shear viscosity versus the weight fraction of the salt appear to be less steep than the one related to the personal care composition comprising sodium laureth(1) sulfate (SLE1S) and cocamidopropyl betaine (CAPB), and sodium chloride as the salt (see Comp. Ex. i).

The rheological profile of the personal care compositions comprising sodium laureth(1) sulfate and cocamidopropyl betaine (CAPB) become more representative to the one of the personal care compositions comprising sodium laureth (3) sulfate, sodium lauryl sulfate (SLS), cocamidopropyl betaine (CAPB) and sodium chloride.

It has been found that when replacing sodium chloride by a salt of Formula I, the salt curve is shifted to a higher salt concentration. Thus, at a lower weight ratio of the salt, the viscosity of the personal care composition is reduced when using a salt has the general formula I. The viscosity maximum and the slope of the salt curve can be reduced.

The salt has the general formula I:

$$M\text{----}A \qquad \text{Formula I}$$

wherein A is an anion selected from the group consisting of sulfate and citrate;
wherein M is a cation selected from the group 1A alkali metal, wherein M is selected from the group consisting of lithium, sodium, potassium, rubidium and cesium, wherein M is selected from the group consisting of lithium, sodium, and potassium;
such salts are trisodium citrate, tripotassium citrate, sodium sulfate and potassium sulfate.

It has been observed that such shift of the curves has not be obtained with metal halide such as potassium chloride, iron II or III chloride and aluminum chloride.

Furthermore, it has been found that when replacing sodium chloride by a salt of Formula I combined with a hydrotrope, specifically a citrate ester such as triethyl citrate, the salt curve is shifted to a higher salt concentration with a significant decrease of the viscosity maximum, which implies easier formation of long micelles and micellar branches (the viscosity maximum is attributed to the formation of micellar branches).

It has been found that the rheological properties of the personal care composition can be optimized upon addition of a salt of Formula I, optionally combined with a citrate ester as a hydrotrope. In that cases, the lathering and dissolution properties are not compromised and even improved.

DETAILED DESCRIPTION OF THE INVENTION

A personal care composition is provided and comprises a surfactant system, wherein the surfactant system comprises:
from 3% to 15% of an anionic surfactant by weight of the composition, wherein the anionic surfactant is sodium laureth(1) sulfate SLE1S,
from 1% to 15% of one or more cosurfactants by weight of the composition;
from 0.10% to 5.0%, from 0.20% to 2.5%, from 0.25% to 1.75%, from 0.50% to 1.75%, of one or more salts of Formula I by total weight of the composition, $$M\text{----}A \qquad \text{Formula I}$$

wherein A is an anion selected from the group consisting of sulfate and citrate;
wherein M is a cation selected from the group 1A alkali metal, wherein M is selected from the group consisting of lithium, sodium, potassium, rubidium and cesium, wherein M is selected from the group consisting of lithium, sodium, and potassium; and wherein the personal care composition does not comprise any metal halide, wherein the metal halide is selected from the group consisting of sodium chloride, potassium chloride, iron II or m chloride and aluminum chloride.

Surfactant System

A personal care composition comprises a surfactant system. The personal care composition may comprise a total amount from 4% to 40%, from 5% to 30%, from 7% to 25% of a surfactant system by weight of the composition.

The surfactant system of the personal care composition comprises from 3% to 15% of an anionic surfactant, from 3% to 12% of an anionic surfactant, from 5% to 10% of an anionic surfactant by total weight of the composition. The anionic surfactant comprises sodium laureth(n) sulfate, hereinafter SLEnS, wherein n which is the average moles of ethoxylation is equal to 1. Thus, the anionic surfactant of the surfactant system is sodium laureth(1) sulfate (SLE1S)

It is understood that a material such as SLEnS, for example, can comprise a significant amount of molecules which have no ethoxylate, 1 mole ethoxylate, 2 mole ethoxylate, 3 mole ethoxylate, and so on in a distribution which can be broad, narrow or truncated from n=0 to 10. Hence, sodium laureth(1) sulfate (SLE1S) can comprise a significant amount of molecules which have no ethoxylate, 1 mole ethoxylate, 3 mole ethoxylate, and so on in a distribution which can be broad, narrow or truncated and still comprise sodium laureth(1) sulfate (SLE1S) where the average of the distribution is 1.

The surfactant system of the personal care composition may not comprise any sodium laureth(n) sulfate (SLEnS), wherein n is the average moles of ethoxylation and wherein n is equal to 0, 2 or 3.

The surfactant system may comprise from 1% to 10% of one or more additional anionic surfactants, from 3% to 9% of one or more additional anionic surfactants, from 5% to 9% of one or more additional anionic surfactants by total weight of the composition.

The one or more additional anionic surfactants may be selected from the group consisting of isethionates, sarcosinates, sulfosuccinates, sulfonates, sulfoacetates, acyl glycinates, acyl alaninates, acyl glutamates, lactates, lactylates, glucose carboxylates, amphoacetates, taurates, and mixtures thereof. In that case, alkyl is defined as a saturated or unsaturated, straight or branched alkyl chain with 7 to 17 carbon atoms, with 9 to 13 carbon atoms. In that case, acyl is defined as of formula R—C(O)—, wherein R is a saturated or unsaturated, straight or branched alkyl chain with 7 to 17 carbon atoms, with 9 to 13 carbon atoms.

Suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride. Non-limiting examples of isethionates can be selected from the group consisting of sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, and mixtures thereof.

Non-limiting examples of sarcosinates can be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroyl-glutamate/lauroylsarcosinate, disodium lauroamphodiacetate, lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and combinations thereof.

Non-limiting examples of sulfonates can include alpha olefin sulfonates, linear alkylbenzene sulfonates, sodium laurylglucosides hydroxypropylsulfonate and combinations thereof.

Non-limiting examples of sulfoacetates can include sodium lauryl sulfoacetate, ammonium lauryl sulfoacetate and combination thereof.

Non-limiting examples of acyl glycinates can include sodium cocoyl glycinate, sodium lauroyl glycinate and combination thereof.

Non-limiting example of acyl alaninates can include sodium cocoyl alaninate, sodium lauroyl alaninate, sodium N-dodecanoyl-1-alaninate and combinations thereof.

Non-limiting examples of acyl glutamates can be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, disodium cocoyl hydrolyzed wheat protein glutamate, potassium cocoyl glutamate, dipotassium cocoyl glutamate, potassium lauroyl glutamate, dipotassium lauroyl glutamate, potassium cocoyl hydrolyzed wheat protein glutamate, dipotassium cocoyl hydrolyzed wheat protein glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallow glutamate, sodium cocoyl/palmoyl/sunfloweroyl glutamate, sodium hydrogenated tallowoyl glutamate, sodium olivoyl glutamate, disodium olivoyl glutamate, sodium palmoyl glutamate, disodium palmoyl glutamate, TEA-cocoyl glutamate, TEA-hydrogenated tallowoyl glutamate, TEA-lauroyl glutamate, and mixtures thereof.

Non-limiting examples of acyl glycinates can include sodium cocoyl glycinate, sodium lauroyl glycinate and combination thereof.

Non-limiting example of lactates can include sodium lactate.

Non-limiting examples of lactylates can include sodium lauroyl lactylate, sodium cocoyl lactylate and combination thereof.

Non-limiting examples of glucose carboxylates can include sodium lauryl glucoside carboxylate, sodium cocoyl glucoside carboxylate and combinations thereof.

Non-limiting examples of alkylamphoacetates can include sodium cocoyl amphoacetate, sodium lauroyl amphoacetate and combination thereof.

Non-limiting examples of acyl taurates can include sodium methyl cocoyl taurate, sodium methyl lauroyl taurate, sodium methyl oleoyl taurate and combination thereof.

Alternatively, the one or more additional anionic surfactants may be selected from the group consisting of ammonium laureth-1 sulfate, triethanolamine laureth-1 sulfate, sodium tridecyl benzene sulfonate, sodium dodecyl benzene sulfonate, sodium lauroyl sarcosinate, sodium lauroyl sarcosinate, sodium cocoyl sarcosinate, sodium lauroyl methyl isethionate, sodium lauroyl isethionate, sodium cocoyl isethionate, sodium lauroyl glycinate, sodium cocoyl glycinate, potassium lauroyl glycinate, potassium cocoyl glycinate, sodium lauroyl glutamate, potassium lauroyl glutamate, sodium cocoyl glutamate, potassium cocoyl glutamate, disodium lauroyl glutamate, dipotassium lauroyl glutamate, disodium cocoyl glutamate, dipotassium cocoyl glutamate, sodium lauroyl lactylate and mixtures thereof.

The personal care composition comprises from 1% to 15% of one or more cosurfactants, from 2% to 8% of one or more cosurfactants, from 2% to 5% of one or more cosurfactants by total weight of the composition. The one or more cosurfactants may be selected from the group consisting of amphoteric surfactants, zwitterionic surfactants, and mixtures thereof.

The personal care composition may include at least one of an amphoteric surfactant and a zwitterionic surfactant. Suitable amphoteric or zwitterionic surfactants can include those described in U.S. Pat. Nos. 5,104,646 and 5,106,609.

Amphoteric surfactants can include those that can be broadly described as derivatives of aliphatic secondary and tertiary amines in which an aliphatic radical can be straight or branched chain and wherein an aliphatic substituent can contain from 8 to 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No.

2,438,091, and products described in U.S. Pat. No. 2,528, 378. The one or more cosurfactants included in the personal care composition described herein may comprise an amphoteric surfactant that is selected from the group consisting of sodium lauroamphoacetate, sodium cocoamphoacetate, disodium lauroamphoacetate, disodium cocodiamphoacetate, and mixtures thereof.

Zwitterionic surfactants suitable for use in the one or more cosurfactants of the personal care composition described herein may include those that are broadly described as derivatives of aliphatic quaternary ammonium, phosphonium, and sulfonium compounds, in which the aliphatic radicals can be straight or branched chains, and wherein one of the aliphatic substituents can contain from 8 to 18 carbon atoms and one can contain an anionic group, e.g., carboxy, sulfonate, sulfate, phosphate, or phosphonate. The zwitterionic surfactant included in the personal care composition described herein may include one or more betaines, including cocoamidopropyl betaine.

Alternatively, the amphoteric or zwitterionic surfactant may be selected from cocamidopropyl betaine, lauramidopropyl betaine, coco-betaine, lauryl betaine, cocoamphoacetate, cocoamphodiacetate, lauroamphoacetate, lauroamphodiacetate, lauramine oxide, sarcosinate, glutamate, lactate and mixtures thereof.

The surfactant system may further comprise one or more zwitterionic surfactants and the zwitterionic surfactant may be a co-surfactant selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

Examples of betaine zwitterionic surfactants may include coco dimethyl carboxymethyl betaine, cocoamidopropyl betaine (CAPB), coco-betaine, lauryl amidopropyl betaine (LAPB), oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

The zwitterionic surfactant can comprise or consist of cocamidopropyl betaine (CAPB), lauramidopropyl betaine (LAPB), and combinations thereof.

The one or more cosurfactants of the personal care composition may comprise a zwitterionic surfactant, a betaine, cocamidopropyl betaine.

The surfactant system may further comprise one or more non-ionic cosurfactants, wherein the one or more non-ionic cosurfactants are selected from the group consisting of glucosides, alkyl amines, alcohol ethoxylates, alkyl polyglucosides, alkyl glucosides, acyl glutamide and mixtures thereof.

The surfactant system may comprise from 1% to 10% of one or more non-ionic cosurfactants, from 3% to 9% of one or more non-ionic cosurfactants, from 5% to 9% of one or more non-ionic cosurfactants by total weight of the composition.

The one or more non-ionic surfactants may be selected from cocoamide monoethanolamine, lauramide monoethanolamine, cocoyl glucoside, lauroyl glucoside, decyl glucoside, and mixtures thereof.

The personal care composition may not comprise any structuring anionic surfactant selecting from the group consisting of sodium trideceth(n) sulfate (STnS) wherein n is between 0 and 3, sodium tridecyl sulfate, sodium $C_{12-13}$ alkyl sulfate, sodium $C_{12-15}$ alkyl sulfate, sodium $C_{11-15}$ alkyl sulfate, sodium $C_{12-18}$ alkyl sulfate, sodium $C_{10-16}$ alkyl sulfate, sodium $C_{12-13}$ pareth sulfate, sodium $C_{12-13}$ pareth-n sulfate, sodium $C_{12-14}$ pareth-n sulfate, and mixtures thereof.

Salt

The personal care composition comprises from 0.10% to 5.0%, from 0.20% to 2.5%, from 0.25% to 1.75%, from 0.50% to 1.75%, of one or more salts of Formula I by total weight of the composition, $$M\text{----}A \qquad \text{Formula I}$$

wherein A is an anion selected from the group consisting of sulfate and citrate; and wherein M is a cation selected from the group 1A alkali metal.

M may be selected from the group consisting of lithium, sodium, potassium, rubidium and cesium. M may be selected from the group consisting of lithium, sodium, and potassium. M may be selected from the group consisting of sodium, and potassium.

The one or more salts are selected from the group consisting of trisodium citrate, tripotassium citrate, sodium sulfate and potassium sulfate.

When sodium chloride is replaced by one or more salts of Formula I, the rheological properties of the personal care composition can be optimized in such way that the corresponding salt curve which is the plot of the zero shear viscosity, namely the viscosity, versus the weight fraction of the salt has a reduced viscosity maximum and a reduced salt curve slope. The salt curve can be shifted towards higher weight fractions of salt. The thickening efficiency of the personal care composition can be improved with an easier formation of long micelles and micellar branches.

Furthermore, the personal care composition can be manufactured on a relatively large industrial scale. The personal care composition can be readily processed since the viscosity can be better controlled.

The personal care composition does not comprise any metal halide, wherein the metal halide is selected from the group consisting of sodium chloride, potassium chloride, iron II or III chloride and aluminum chloride.

Hydrotrope

The personal care composition may comprise from 0.10% to 5.0%, from 0.50% to 3.0%, from 0.75% to 2.0%, from 1.0% to 1.75%, of one or more hydrotropes, by weight of the composition.

The one or more hydrotropes of the personal care composition may comprise one or more citrate esters selected from the group consisting of trimethyl citrate, triethyl citrate, tripropyl citrate, tributyl citrate, tripentyl citrate, trihexyl citrate, tricyclohexyl citrate, triisopropyl citrate, triisobutyl citrate, trisecbutyl citrate, triisopentyl citrate, tertiobutyldimethyl citrate, and combinations thereof.

The one or more hydrotropes of the personal care composition may comprise one or more citrate esters selected from the group consisting of trimethyl citrate, triethyl citrate, tripropyl citrate, tributyl citrate and combinations thereof.

The one or more hydrotropes of the personal care composition may comprise a citrate ester selected from triethyl citrate.

The one or more hydrotropes of the personal care composition may comprise one or more salts of citrate as defined hereinabove, wherein the cation M is selected from the group consisting of sodium and potassium; and wherein the one or more hydrotropes comprise one or more citrate esters as defined hereinabove.

The personal care composition may comprise the one or more salts of Formula I comprising trisodium citrate and the one or more hydrotropes comprising triethyl citrate.

The one or more hydrotropes of the personal care composition may comprise a salt of citrate, wherein the cation M is selected from the group consisting of sodium and potassium; and wherein the one or more hydrotropes comprise triethyl citrate; wherein the one or more salts of Formula I comprise trisodium citrate and wherein the one or more hydrotropes comprise triethyl citrate.

When replacing in a personal care composition, sodium chloride by one or more salts of Formula I combined with one or more citrate esters such as triethyl citrate, the salt curve is shifted to a higher salt concentration with a significant decrease of the viscosity maximum, which implies easier formation of long micelles and micellar branches. The rheological properties of the personal composition have been found to be even more improved when sodium chloride is replaced with one or more salts of Formula I combined with one or more citrate esters, than only with one or more salts of Formula I with the surfactant system of the present invention.

Liquid Carrier

Inclusion of an appropriate quantity of a liquid carrier can facilitate the formation of the personal care composition having an appropriate liquid viscosity and rheology. The personal care composition may include from 40% to 95%, of a liquid carrier, from 55% to 90%, and from 60% to 80%, by weight of the composition.

A liquid carrier may be water, or may be a miscible mixture of water and organic solvent. Alternatively, a liquid carrier may be water with minimal or no significant concentrations of organic solvent, except as otherwise incidentally incorporated into the composition as minor ingredients of other essential or optional components. Suitable organic solvents may include water solutions of lower alkyl alcohols and polyhydric alcohols. Useful lower alkyl alcohols include monohydric alcohols having 1 to 6 carbon atoms, such as ethanol and isopropanol. Exemplary polyhydric alcohols include propylene glycol, hexylene glycol, glycerin, and propane diol.

Optional Ingredients

As can be appreciated, the compositions described herein may include a variety of optional components to tailor the properties and characteristics of the composition. As can be appreciated, suitable optional components are well known and can generally include any components which are physically and chemically compatible with the essential components of the compositions described herein. Optional components should not otherwise unduly impair product stability, aesthetics, or performance. Individual concentrations of optional components can generally range from 0.001% to 10%, by weight of the composition. Optional components can be further limited to components which will not impair the clarity of a translucent composition.

Optional components may include, but are not limited to, conditioning agents (including hydrocarbon oils, fatty esters, silicones), cationic polymers, anti-dandruff actives, and chelating agents. Additional suitable optional ingredients include but are not limited to encapsulated and non-encapsulated perfumes or fragrances, colorants, particles, anti-microbials, foam boosters, anti-static agents, moisturizing agents, propellants, self-foaming agents, pH adjusting agents and buffers, preservatives, pearlescent agents, opacifiers, sensates, suspending agents, solvents, diluents, antioxidants, vitamins and combinations thereof.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

Forms and Uses

Product Form

The composition may be presented in typical personal care formulations. They may be in the form of solutions, dispersion, emulsions, foams, and other delivery mechanisms. The composition may be a micellar composition.

The composition may be liquid or solid. The composition may be the form of a shower or bath cream, a body wash or foaming body wash, gel, emulsion, oil, mousse or spray.

The composition in the form of a foam may have a density of from 0.02 g/cm$^3$ to 0.2 g/cm$^3$, alternatively from 0.025 g/cm$^3$ to 0.15 g/cm$^3$, alternatively from 0.05 g/cm$^3$ to 0.15 g/cm$^3$. The density can be measured with the Foam Density & Foam Volume Method, described hereafter.

Foam Dispenser

The personal care composition may be stored and dispensed from a mechanical pump foam dispenser that may comprise a reservoir for holding the composition and a foam engine. The reservoir may be made from any suitable material selected from the group consisting of plastic, metal, alloy, laminate, and combinations thereof. The reservoir may be for one-time use. The reservoir may be removable from the mechanical pump foam dispenser. Alternatively, the reservoir may be integrated with the mechanical pump foam dispenser. There may be two or more reservoirs.

The reservoir may be comprised of a material selected from the group consisting of rigid materials, flexible materials, and combinations thereof. The reservoir can be made from plastic.

Suitable foam dispenser available from Albéa can include tabletop models T1, WRT4, WRT6, and handheld models M3, WRM3, WRD4, F2, F3 and G3 with a L value of 7, 9 or 11, wherein L value is the air to liquid ratio.

The composition may be stored and dispensed from a squeeze foam dispenser. An example of squeeze foamer is EZ'R available from Albéa.

Non-limiting examples of suitable pump dispensers include those described in WO 2004/078903, WO 2004/078901, and WO 2005/078063 and may be supplied by Albea (60 Electric Ave., Thomaston, Conn. 06787 USA) or Rieke Packaging Systems (500 West Seventh St., Auburn, Ind. 46706).

The composition and/or the dispenser may be free or substantially free of a propellant, for instance aerosol propellants.

Uses

An aspect of the present invention is related to the use of a personal care composition comprising:

(a) a surfactant system, wherein the surfactant system comprises:

from 3% to 15% of an anionic surfactant by weight of the composition, wherein the anionic surfactant is sodium laureth(1) sulfate SLE1S, from 2% to 15% of one or more cosurfactants by weight of the composition;

(b) from 0.10% to 5.0%, from 0.20% to 2.5%, from 0.25% to 1.75%, from 0.50% to 1.75%, of one or more salts of Formula I by total weight of the composition, $$M\text{----}A \qquad \text{Formula I}$$

wherein A is an anion selected from the group consisting of sulfate and citrate;
wherein M is a cation selected from the group 1A alkali metal, wherein M is selected from the group consisting of lithium, sodium, potassium, rubidium and cesium, wherein M is selected from the group consisting of lithium, sodium, and potassium; and
wherein the personal care composition does not comprise any metal halide, wherein the metal halide is selected from the group consisting of sodium chloride, potassium chloride, iron II or III chloride and aluminum chloride for decreasing the viscosity maximum and the slope value of the curve of the viscosity of the personal care composition versus the weight amount of the one or more salts by weight of the composition.

The personal care composition may be used for helping processability and personal care composition stability.

The one or more salts of Formula I as defined hereinabove, optionally in combination with the one or more hydrotropes as defined hereinabove in the present personal care composition may be used for improving the rheological properties of the personal care composition.

The one or more salts of Formula I as defined hereinabove, optionally in combination with the one or more hydrotropes as defined hereinabove in the present personal care composition may be used for improving the lathering and dissolution properties of the personal care composition.

Test Methods

It is understood that the test methods that are disclosed in the Test Methods Section of the present application should be used to determine the respective values of the parameters of Applicants' invention as such invention is described and claimed herein.

Viscosity Test Method

The viscosity of the composition is measured using a Brookfield Viscometer (model RVDVII) with a CPE-41 Spindle with temperature control. The system parameters are listed below:
Temperature: 25° C.
Spindle Rotation Speed: 1 RPM ($2 \ s^{-1}$)
Gap: 13 micron
Duration: 2 minutes
Cone Angle: 3°
TAN Delta Test Method Determined by Oscillatory Rheology Tests To measure the viscous (G") and elastic (G') moduli (loss and storage modulus) of a composition, a AR G2 Rheometer (TA Instruments, DE, USA) is used and is equipped with 1 degree cone upper geometry with a diameter of 40 mm and a flat plate lower geometry equipped with Pletier heating/cooling to control temperature. Measurement can be conducted by placing approximately 1 gram of the composition onto a lower test geometry and lowering the upper geometry to the desired gap of 27 microns, wiping away any excess of the composition to create an even surface around the edge of the geometry. The oscillatory test is conducted over frequency range of 0.01 to 100 radians per second, collecting 10 data points per decade, using a constant oscillatory stress of 0.1 Pa utilizing and a set temperature of 25° C. Oscillation stress sweeps are run to generate the elastic modulus or storage modulus (G'), the viscous modulus or loss modulus (G") and Tan Delta which is calculated as the follows:

$$\tan\delta = \frac{G''}{G'}$$

Foam Density and Foam Volume

Foam density is measured by placing a 100 mL beaker onto a mass balance, tarring the mass of the beaker and then dispensing product from the aerosol container into the 100 mL beaker until the volume of the foam is above the rim of the vessel. The foam is made level with the top of the beaker by scraping a spatula across it within 10 seconds of dispensing the foam above the rim of the vessel. The resulting mass of the 100 mL of foam is then divided by the volume (100) to determine the foam density in units of g/mL.

Foam volume is measured by placing a weigh boat onto a mass balance, tarring the mass of the weigh boat and then dispensing the desired amount of product from the aerosol container. The grams of foam dispensed is determined and then divided by the density of foam as determined from the Foam Density methodology to reach a volume of foam in mL or $cm^3$.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

The following examples were prepared:
Compositions (Wt. %)

| Ingredients | Comp. Ex. 1 | Ex. 1 | Ex. 2 | Ex. 3 | Ex. 4 | Ex. 5 | Ex. 6 | Ex. 7 | Ex. 8 |
|---|---|---|---|---|---|---|---|---|---|
| Water | 61.48 | 61.48 | 59.48 | 61.23 | 60.23 | 62.23 | 60.73 | 62.23 | 61.48 |
| SLE1S (28% active)[1] | 28.57 (8%) | 28.57 (8%) | 33.57 (9.4%) | 28.57 (8%) | 33.57 (9.4%) | 28.57 (8%) | 33.57 (9.4%) | 28.57 (8%) | 28.57 (8%) |
| CAPB (30% active)[2] | 6.67 (2%) | 6.67 (2%) | — | 6.67 (2%) | — | 6.67 (2%) | — | 6.67 (2%) | 6.67 (2%) |
| LAPB (30% active)[3] | — | — | 3.67 (1.1%) | — | 3.67 (1.1%) | — | 3.67 (1.1%) | — | — |
| Sodium Benzoate[4] | 0.25 | 0.25 | 0.25 | 0.25 | 0.25 | 0.25 | 0.25 | 0.25 | 0.25 |
| Methylchloroisothiazolinone/ Methylisothiazolinone (MCIT/MIT)[5] | 0.03 | 0.03 | 0.03 | 0.03 | 0.03 | 0.03 | 0.03 | 0.03 | 0.03 |

-continued

| Ingredients | Comp. Ex. 1 | Ex. 1 | Ex. 2 | Ex. 3 | Ex. 4 | Ex. 5 | Ex. 6 | Ex. 7 | Ex. 8 |
|---|---|---|---|---|---|---|---|---|---|
| Fragrance | 1.00 | 1.00 | 1.00 | 2.00 | 1.00 | 1.50 | 1.00 | 1.00 | 1.00 |
| Disodium EDTA[6] | 0.10 | 0.10 | 0.10 | 0.10 | 0.10 | 0.10 | 0.10 | 0.10 | 0.10 |
| Citric Acid[7] | 0.15 | 0.15 | 0.15 | 0.15 | 0.15 | 0.15 | 0.15 | 0.15 | 0.15 |
| NaCl[8] | 1.75 | — | — | — | — | — | — | — | — |
| Trisodium citrate[9] | — | 1.75 | 1.75 | — | — | — | — | — | 1.25 |
| Sodium sulfate[10] | — | — | — | 1.00 | 1.00 | — | — | — | — |
| Tripotassium citrate[11] | — | — | — | — | — | 0.50 | 0.50 | — | — |
| Potassium sulfate[12] | — | — | — | — | — | — | — | 1.00 | — |
| Triethyl citrate[13] | — | — | — | — | — | — | — | — | 0.50 |

Definitions of Components
[1]Sodium Laureth-1 Sulfate; Supplier Procter & Gamble Co.
[2]Cocamidopropyl Betaine; Supplier BASF
[3]Laurylamidopropyl Betaine; Supplier BASF
[4]Purox S Grains; Supplier Emerald Kalama Chemical
[5]Kathon; Supplier Rohm & Haas
[6]Disodium Ethylene Diamine Tetraacetic Acid; Supplier Akzo Nobel
[7]Citric Acid; Supplier Cargill
[8]Sodium Chloride; Supplier Morton International
[9]Trisodium citrate; Supplier Cargill
[10]Sodium sulfate; Supplier Saskatchewan Minerals
[11]Tripotassium citrate; Supplier Cargill
[12]Potassium sulfate; Supplier Saskatchewan Minerals
[13]Triethyl citrate; Supplier Cargill Method of Preparation The above compositions of "Comp. Ex. 1, Ex. 1" through "Ex. 8" were prepared by the following method according to the proportions provided in the Table hereinabove.

Water was first added to a container along with a magnetic stir bar. Sodium Laureth(1) Sulfate, Cocamidopropyl Betaine, or Laurylamidopropyl Betaine when applicable were added. The system was mixed at 300-400 rpm for 2 minutes. Sodium benzoate, Methylchloroisothiazolinone/Methylisothiazolinone, fragrance, EDTA, and citric acid were added and the system mixed for an additional 2 minutes at 300-400 rpm. Then, sodium chloride or the respective salt and/or hydrotrope was added and the system mixed until thickened; 1 minute at 300-400 rpm.

Experimental

Rheological Experiments

The following compositions were prepared according to the general composition of Ex. 1 comprising 8 wt. % active of SLE1S and 2 wt. % active of CAPB, hence a 10 wt. % of total surfactants.

Compositions (Wt. %)

| Ingredients | Ex. X |
|---|---|
| Water | qsp |
| SLE1S (28% active)[1] | 28.57 |
| | (8%) |
| CAPB (30% active)[2] | 6.67 |
| | (2%) |
| Sodium Benzoate[4] | 0.25 |
| Methylchloroisothiazolinone/Methylisothiazolinone (MCIT/MIT)[5] | 0.03 |
| Fragrance | 1.00 |
| Disodium EDTA[6] | 0.10 |
| Citric Acid[7] | 0.15 |
| SALT | x % wt. |

For each composition, a salt has been tested:

| SALT | |
|---|---|
| NaCl[8] | Comp. Ex. i |
| Trisodium citrate[9] | Ex. A |
| Sodium sulfate[10] | Ex. B |
| Tripotassium citrate[11] | Ex. C |
| NaCl[8] + Triethyl citrate[13] | Ex. E |
| Trisodium citrate[9] + Triethyl citrate[13] | Ex. F |

A control composition CØ has been prepared. The control composition CØ includes another surfactant system comprising 10% wt. of a mixture of sodium laureth-3 sulfate (SLE3S), sodium lauryl sulfate (SLS) and cocoamidopropyl betaine (CAPB).

| Ingredients | Control CØ |
|---|---|
| Water | qsp |
| SLE3S (28% active)[1] | 23.20 |
| | (6.5%) |
| SLS (29% active)[14] | 8.60 |
| | (2.5%) |
| CAPB (30% active)[2] | 3.33 |
| | (1.0%) |
| Sodium Benzoate[4] | 0.25 |
| Methylchloroisothiazolinone/Methylisothiazolinone (MCIT/MIT)[5] | 0.03 |
| Fragrance | 2.00 |
| Disodium EDTA[6] | 0.10 |
| Citric Acid[7] | 0.15 |
| NaCl | x % wt. |

Definitions of Components
* 14 Sodium Lauryl Sulfate; Supplier Procter & Gamble Co.

Methodology for the Rheological Experiments:

An AR-G2 rotational rheometer with an acrylic cone and plate (to minimize inertial effects) was used to measure the zero shear viscosity at constant shear rate, and rheological moduli at constant shear stress but varying frequency.

We sampled 25 data points per decade at high frequency and 10 data points per decade at low frequency to obtain enough information for model fitting in a reasonable time. Samples were freshly loaded each time and a solvent trap was used to prevent sample evaporation near the edge. All rheological measurements were performed within the linear viscoelastic regime at room temperature, close to 25° C., unless otherwise specified. Randomly selected samples were remeasured and the standard deviation of rheological measurements was found to be less than 3%.

Figure 1:
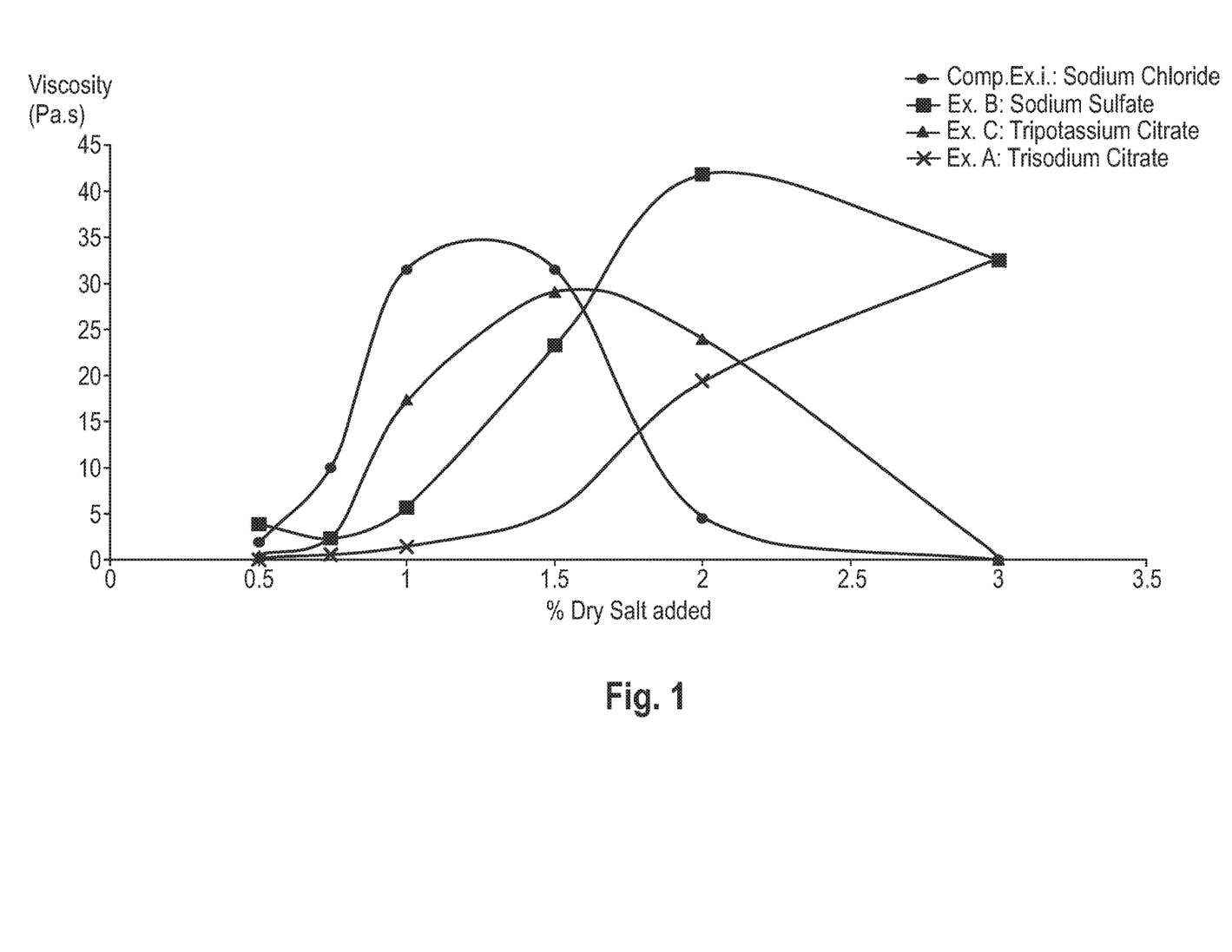
FIG. 1 represents the "salt curves" by plotting the zero shear viscosity versus the weight fraction of the salt for personal care compositions differing by the nature of the salt according to the present invention for Ex. A with trisodium citrate, Ex. B with sodium sulfate and Ex. C with tripotassium citrate, versus Comp. Ex. i. with sodium chloride.
Figure 2:
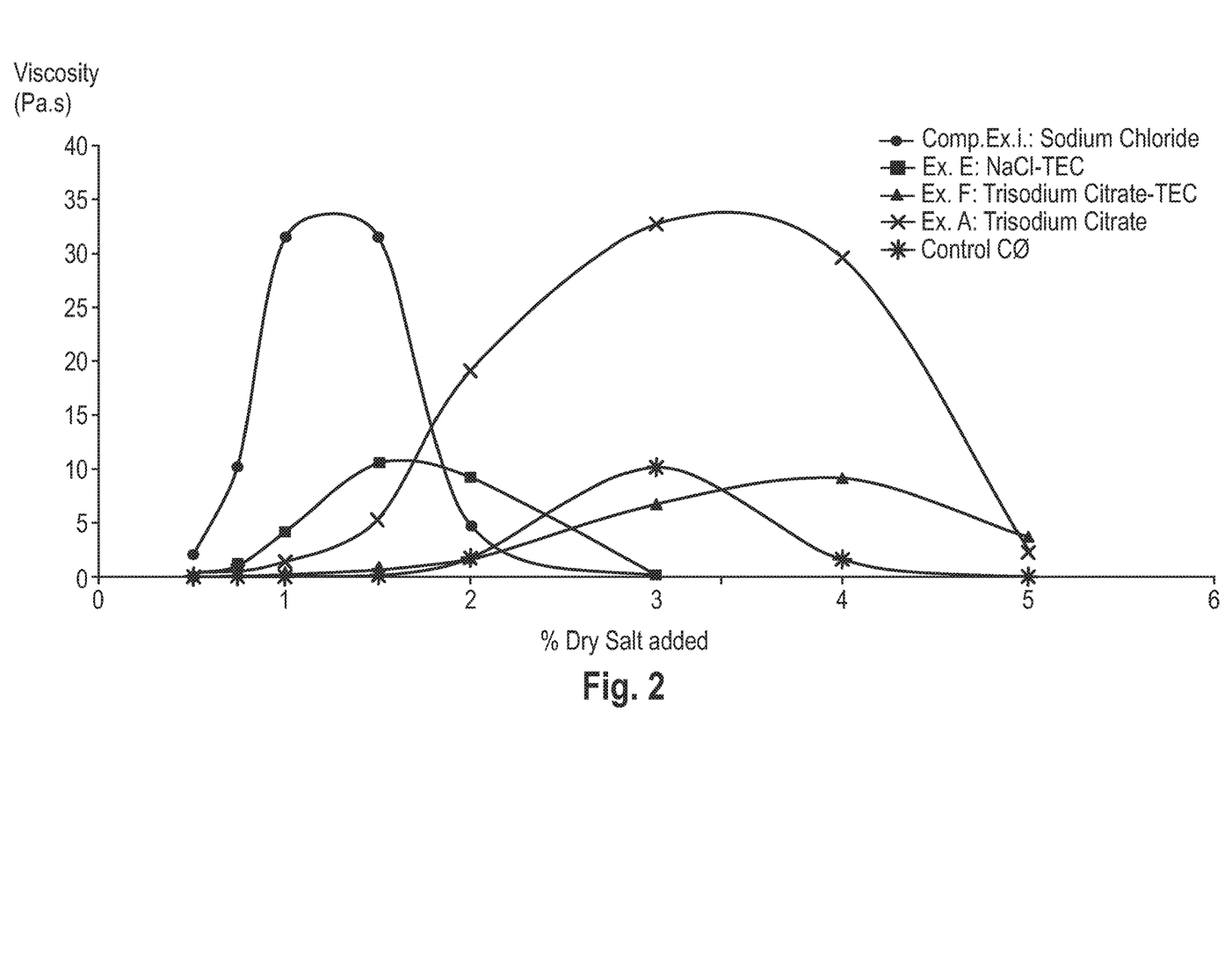
FIG. 2 represents the "salt curves" by plotting the zero shear viscosity versus the weight fraction of the salt for personal care compositions differing by the nature of the salt and the hydrotrope when applicable according to the present invention for Ex. A with trisodium citrate, Ex. F with trisodium citrate and triethyl citrate, versus Ex. E with sodium chloride and triethyl citrate, Comp. Ex. i. with sodium chloride and Control CØ.

Results:

Plots of the zero shear viscosity versus the weight fraction of the salt (e.g. NaCl), referred to as "salt curves" for the Comp. Ex. i, Exs. A-C are shown in FIG. 1 and for the Control CØ, Comp. Ex. i, Exs. A, E and F are shown in FIG. 2.

Control CØ

The salt curve of Control CØ comprising 10% wt. of a surfactant system including sodium laureth-3 sulfate (SLE3S), sodium lauryl sulfate (SLS) and cocoamidopropyl betaine (CAPB) (solid lines with special symbol *), the zero shear viscosity (simply called "viscosity" in the following discussion) increases with sodium chloride salt concentration and reaches a maximum (10 Pa·s at 3.0% wt. NaCl), followed by a decrease at high salt concentration.

Comparative Ex. i.

Now, when replacing the surfactant system of Control CØ with 10% wt. of a surfactant system including sodium laureth-1 sulfate (SLE1S) and cocoamidopropyl betaine (CAPB) (solid lines with circles) and still comprising sodium chloride as a salt, the "viscosity" increases drastically with sodium chloride salt concentration and reaches a maximum (34 Pa·s with only 1.5% wt. NaCl), followed by a decrease at 2% wt. NaCl.

Comparison of Salt of Formula I Versus NaCl

The salt curves for the same surfactant system as Comparative Ex. i, however using a salt differing from sodium chloride, and optionally with a hydrotrope have been generated in FIG. 1 and FIG. 2.

The objective is to obtain a similar rheology profile than Control CØ having a maximum of 10 Pa·s at a relatively higher level of salt in comparison to the relatively steeper curve of Comparative Ex. i comprising a different surfactant system (SLE1S+CAPB).

From the above figures, the salt curves initially show nearly exponential increases in viscosity at low salt concentration, then a linear dependence, and finally a concave-downward shape near the maximum.

As shown in FIG. 1, it is possible to get a decrease of viscosity at an operated level of 1% wt. salt when the salt is of Formula I: M----A, wherein A is an anion selected from the group consisting of sulfate and citrate; and wherein M is a cation selected from the group 1A alkali metal.

TABLE 1

Comparison of Salts (with 1% Level of Salt)

| | Selected salts | Viscosity |
|---|---|---|
| Comp. Ex. i | NaCl (SLE1S + CAPB) | 28 Pa·s |
| Ex. A | Trisodium Citrate | 1 Pa·s |
| Ex. B | Sodium Sulfate | 6 Pa·s |
| Ex. C | Tripotassium Citrate | 12 Pa·s |
| Control CØ | NaCl (SLE3S, SLS + CAPB) | 0.25 Pa·s |

It has been found that the viscosity of the personal care composition can be significantly decreased at 1% salt when replacing sodium chloride by another salt of Formula I.

TABLE 2

Comparison of Salts (in terms of viscosity maximum and salt curve slope)

| | Select Salts | Viscosity Max (Pa·s) | Salt Curve Slope (Pa·s/% salt) |
|---|---|---|---|
| Comp. Ex. i | NaCl (SLE1S + CAPB) | 35 | 88 |
| Ex. A | Trisodium Citrate | 35 | 13 |
| Ex. C | Tripotassium Citrate | 30 | 24 |
| Ex. B | Sodium Sulfate | 42 | 34 |
| Control CØ | NaCl (SLE3S, SLS + CAPB) | 10 | 8 |

The replacement of sodium chloride with a salt of formula I can help to reduce the viscosity maximum and the slope of the salt curve. As shown in Table 2, citrate and sulfate salts are effective as changing the viscosity profile in terms of salt curve slope. Tripotassium citrate can help to decrease the viscosity maximum and the salt curve slope.

It has been found that only Group 1A metals are the most effective as the counter ions. In other words, only monovalent metals lithium, sodium, potassium, rubidium and cesium etc. shall be selected as the cation M of the salt of Formula I whereas other multi-valent metals such as calcium, magnesium, barium, copper (II), iron (II or III), cobalt, zinc and aluminum or non-Group 1A mono-valent ions such as silver, copper (I), ammonium do not work well. These other salts either do not form any micellar structure or form limited micellar structure and/or impart strong odor and/or color to the personal care composition.

Influence of the Presence of a Hydrotrope

As shown in FIG. 2, it is possible to get a similar viscosity maximum that Control CØ but at a lower operated level of 1.5% wt. salt when replacing sodium chloride with a hydrotrope comprising citrate esters such as triethyl citrate (Ex. E).

TABLE 3

Comparison of Hydrotropes (Maximum Viscosity)

| | Selected salts | Viscosity |
|---|---|---|
| Comp. Ex. i | NaCl (SLE1S + CAPB) | 34 Pa·s (at 1.5% salt) |
| Ex. A | Trisodium Citrate | 34 Pa·s (at 3.3% salt) |
| Ex. E | Sodium chloride + triethyl citrate | 11 Pa·s (at 1.5% salt) |
| Ex. F | Trisodium Citrate + Triethyl Citrate | 10 Pa·s (at 4.0% salt) |
| Control CØ | NaCl (SLE3S, SLS + CAPB) | 10 Pa·s (at 3.0% salt) |

When replacing sodium chloride with trisodium citrate (see Ex. A), the viscosity of the composition can be reduced at a relatively low level of salt (below 2% wt.), however, the salt curve remains relatively steeper at a higher level of salt (above 3% wt.).

When using a citrate ester as a hydrotrope such as triethyl citrate, the maximum viscosity obtained for the control is then reached but at a lower level of salt (at 1.5% salt, Ex. E).

However, it has been surprisingly found that when combining trisodium citrate and triethyl citrate (Ex. F), the maximum viscosity obtained for the control is then reached but at a higher level of salt (at 4% salt, Ex. F) than when using sodium chloride and triethyl citrate (Ex. E), even more than Control CØ.

TABLE 4

Comparison of Salts with hydrotropes
(in terms of viscosity maximum and salt curve slope)

| | Select Salts | Viscosity Max (Pa · s) | Salt Curve Slope (Pa · s/% salt) |
|---|---|---|---|
| Comp. Ex. i | NaCl (SLE1S + CAPB) | 35 | 88 |
| Ex. F | Trisodium Citrate + Triethyl Citrate | 10 | 5 |
| Control CØ | NaCl (SLE3S, SLS + CAPB) | 10 | 8 |

The replacement of sodium chloride with a salt of Formula I and a hydrotrope such as a citrate ester has also been found to reduce not only the viscosity maximum but also the slope of the salt curve. As shown in Table 4, the combination of trisodium citrate with a citrate ester such as triethyl citrate can help to optimize the rheological properties even better than with the surfactant system comprising sodium laureth (3) sulfate (SLE3S), sodium lauryl sulfate (SLS) and cocamidopropyl betaine (CAPB) (Control CØ).

The salt curve of Example F comprising trisodium citrate and triethyl citrate is also shifted to a higher salt concentration in comparison to the salt curve of Example E comprising sodium chloride and triethyl citrate, and even more than the salt curve of Control CØ, with a lower viscosity maximum and a lower salt curve slope. This implies easier formation of long micelles and micellar branches. The thickening efficiency of the surfactant system comprising sodium laureth(1) sulfate (SLE1S) and cocamidopropyl betaine (CAPB) has been optimized accordingly.

Other solvents or hydrotropes have been investigated and included glycerin, sorbitol, triglycerides, alcohols, glycols, polyglycols (e.g. polyethylene glycol or PEGs), or fatty esters (e.g. isopropyl myristate). These materials either had no impact on the salt curve or completely disrupted the thickening effectiveness which results in extremely low viscosity.

CONCLUSION

It has been found that when replacing sodium chloride by a salt of Formula I, the salt curve is shifted to a higher salt concentration with a relatively less steep profile.

Furthermore, it has been found that when replacing sodium chloride by a salt of Formula I combined with a citrate ester, the salt curve is shifted to a higher salt concentration with a relatively lower viscosity maximum and a lower salt curve slope, which implies easier formation of long micelles and micellar branches.

It has been found that the rheological property of the personal care composition can be optimized upon addition of a salt of Formula I, optionally combined with a citrate ester as a hydrotrope.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
    (a) a surfactant system, wherein the surfactant system comprises:
        from about 3% to about 15% of an anionic surfactant by weight of the composition, wherein the anionic surfactant is sodium laureth(1) sulfate SLE1S, from about 1% to about 15% of one or more cosurfactants by weight of the composition comprise a zwitterionic surfactant;
    (b) from about 0.10% to about 5.0%, of one or more salts of Formula I by total weight of the composition and wherein the personal care composition does not comprise any sodium laureth(n) sulfate SLEnS, where n is the average moles of ethoxylation, wherein n is 0, 2 or 3, $$M\text{----}A \qquad \text{Formula I}$$

wherein A is an anion selected from the group consisting of sulfate and citrate;
wherein M is a cation selected from the group 1A alkali metal; and
wherein the personal care composition does not comprise sodium chloride, potassium chloride, iron II chloride, iron III chloride, or aluminum chloride;
wherein the personal care composition comprises from 0.10% to 5.0%, of one or more hydrotropes, by weight of the composition;
wherein the one or more salts of Formula I comprise one or more salts of citrate, wherein the cation M is selected from the group consisting of sodium and potassium; and wherein the one or more hydrotropes comprise one or more citrate esters selected from the group consisting of trimethyl citrate, triethyl citrate, tripropyl citrate, tributyl citrate, tripentyl citrate, trihexyl citrate, tricyclohexyl citrate, triisopropyl citrate, triisobutyl citrate, trisecbutyl citrate, triisopentyl citrate, tertiobutyldimethyl citrate and combinations thereof;
wherein the total amount of one or more salts of Formula I ranges from 0.10% to 5.0%, by total weight of the composition.

2. The personal care composition of claim 1, wherein the surfactant system of the personal care composition further comprises from about 1% to about 10% of one or more additional anionic co-surfactants by total weight of the composition, wherein the one or more additional anionic co-surfactants are selected from the group consisting of isethionates, sarcosinates, sulfosuccinates, sulfonates, sulfoacetates, acyl glycinates, acyl alaninates, acyl glutamates, lactates, lactylates, glucose carboxylates, amphoacetates, taurates, and mixtures thereof.

3. The personal care composition of claim 1, wherein the surfactant system of the personal care composition further comprises from about 1% to about 10% of one or more additional anionic co-surfactants by total weight of the composition, wherein the one or more additional anionic co-surfactants are selected from the group consisting of ammonium laureth-1 sulfate, triethanolamine laureth-1 sulfate, sodium tridecyl benzene sulfonate, sodium dodecyl benzene sulfonate, sodium lauroyl sarcosinate, sodium lauroyl sarcosinate, sodium cocoyl sarcosinate, sodium lauroyl methyl isethionate, sodium lauroyl isethionate, sodium cocoyl isethionate, sodium lauroyl glycinate, sodium cocoyl glycinate, potassium lauroyl glycinate, potassium cocoyl glycinate, sodium lauroyl glutamate, potassium lauroyl glutamate, sodium cocoyl glutamate, potassium cocoyl glutamate, disodium lauroyl glutamate, dipotassium lauroyl glutamate, disodium cocoyl glutamate, dipotassium cocoyl glutamate, sodium lauroyl lactylates, and mixtures thereof.

4. The personal care composition of claim 1, wherein the surfactant system of the personal care composition further comprises from about 1% to about 10% of one or more non-ionic co-surfactants by total weight of the composition, wherein the one or more non-ionic co-surfactants are selected from the group consisting of glucosides, alkyl amines, alcohol ethoxylates, alkyl polyglucosides, alkyl glycosides, acyl glutamide and mixtures thereof.

5. The personal care composition according to claim 1, wherein the personal care composition does not comprise any structuring anionic surfactant selecting from the group consisting of sodium trideceth(n) sulfate wherein n is between 0 and 3, sodium tridecyl sulfate, sodium $C_{12\text{-}13}$ alkyl sulfate, sodium $C_{12\text{-}15}$ alkyl sulfate, sodium $C_{11\text{-}15}$ alkyl sulfate, sodium $C_{12\text{-}18}$ alkyl sulfate, sodium $C_{10\text{-}16}$ alkyl sulfate, sodium $C_{12\text{-}13}$ pareth sulfate, sodium $C_{12\text{-}13}$ pareth-n sulfate, sodium $C_{12\text{-}14}$ pareth-n sulfate, and mixtures thereof.

6. The personal care composition according to claim 1, wherein the personal care composition is liquid or solid; and is the form of a shower cream, bath cream, a body wash, foaming body wash, gel, emulsion, oil, mousse, or spray.

7. The personal care composition of claim 1, wherein the personal care composition does not comprise any metal halide.

* * * * *